(12) United States Patent
Corbella et al.

(10) Patent No.: US 7,427,406 B2
(45) Date of Patent: Sep. 23, 2008

(54) AEROSOLS

(75) Inventors: Alberto Corbella, Como (IT); Christian Somigliana, Torno (IT)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 830 days.

(21) Appl. No.: 10/332,286

(22) PCT Filed: Jun. 30, 2001

(86) PCT No.: PCT/EP01/07514

§ 371 (c)(1),
(2), (4) Date: Aug. 11, 2003

(87) PCT Pub. No.: WO02/03927

PCT Pub. Date: Jan. 17, 2002

(65) Prior Publication Data

US 2004/0028614 A1    Feb. 12, 2004

(30) Foreign Application Priority Data

Jul. 7, 2000   (DE) .............................. 100 33 022

(51) Int. Cl.
*A61K 8/00*    (2006.01)
*A61K 8/02*    (2006.01)
*A61K 8/30*    (2006.01)
*A61K 8/92*    (2006.01)
*A61K 8/37*    (2006.01)
*A61K 31/265*  (2006.01)
*A61K 9/12*    (2006.01)

(52) U.S. Cl. ......................... 424/401; 424/43; 424/45; 514/512

(58) Field of Classification Search .............. 424/401, 424/489, 46
See application file for complete search history.

(56) References Cited

U.S. PATENT DOCUMENTS

| | | | |
|---|---|---|---|
| 3,996,153 A | 12/1976 | Heeb et al. | |
| 4,172,887 A | 10/1979 | Vanlerberghe et al. | |
| 5,098,886 A | 3/1992 | Narula et al. | |
| 5,705,169 A | 1/1998 | Stein et al. | |
| 5,730,960 A | 3/1998 | Stein et al. | |
| 5,945,091 A | 8/1999 | Habeck et al. | |
| 6,193,960 B1 | 2/2001 | Metzger et al. | |
| 6,231,837 B1 * | 5/2001 | Stroud et al. | 424/59 |
| 6,482,418 B1 * | 11/2002 | Loehl et al. | 424/401 |
| 6,620,409 B2 | 9/2003 | Bossmann et al. | |
| 6,916,465 B2 | 7/2005 | Panzer et al. | |
| 2003/0053970 A1 | 3/2003 | Bruening et al. | |

FOREIGN PATENT DOCUMENTS

| | | |
|---|---|---|
| DE | 1 165 574 A | 8/1960 |
| DE | 2 024 051 A | 12/1971 |
| DE | 197 12 033 A1 | 9/1998 |
| DE | 197 56 377 A1 | 6/1999 |
| DE | 198 58 812 A1 | 6/2000 |
| DE | 100 02 643 A1 | 7/2001 |
| EP | 0 693 471 B1 | 1/1996 |
| EP | 0 694 521 B1 | 1/1996 |
| EP | 0 816 322 A1 | 1/1998 |
| EP | 0 818 450 A1 | 1/1998 |
| EP | 0 884 045 A1 | 12/1998 |
| EP | 1 103 246 A1 | 5/2001 |
| EP | 1 121 925 A1 | 8/2001 |
| FR | 2 252 840 A1 | 8/1975 |
| GB | 962919 A | 7/1964 |
| GB | 1 333 475 A | 10/1973 |
| WO | WO 92/22282 A1 | 12/1992 |
| WO | WO 94/01511 A1 | 1/1994 |
| WO | WO 95/16824 A1 | 6/1995 |
| WO | WO 95/35411 A1 | 12/1995 |
| WO | WO 95/35412 A1 | 12/1995 |
| WO | WO 96/24723 A1 | 8/1996 |
| WO | WO 97/29170 A1 | 8/1997 |
| WO | WO 97/46205 A2 | 12/1997 |
| WO | WO 97/47282 A1 | 12/1997 |
| WO | WO 01/22933 A1 | 4/2001 |
| WO | WO 01/47480 A1 | 7/2001 |
| WO | WO 01/52806 A1 | 7/2001 |
| WO | WO 01/70191 A1 | 9/2001 |

OTHER PUBLICATIONS

"Tinplate builds up a lead in the European aerosol can market", Aerosol and Spray Report, vol. 36, No. 3, (1997), pp. 10-12.
"CAS News", Aerosol Spray Report, vol. 36, No. 9, (1997), pp. 80-81.
J. Wilhelm, "IGA Annual Report 1996", Aersol and Spray Report, vol. 36, No. 6, (1997), pp. 34-39.
Kirk-Othmer, Encyclopedia of Chemical Technology, 4th Edition, vol. 1, pp. 670-685.

(Continued)

*Primary Examiner*—Johann Richter
*Assistant Examiner*—James H Alstrum Acevedo

(57) ABSTRACT

Cosmetic and/or pharmaceutical preparations comprising (a) a carbonate of the formula (I):

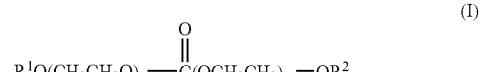

wherein $R^1$ is a linear alkyl and/or alkenyl group having from 6 to 22 carbon atoms, a 2-ethylhexyl, isotridecyl or isostearyl group or a group derived from a polyol having from 2 to 15 carbon atoms and at least two hydroxyl groups; $R^2$ has the same meaning as $R^1$ or is an alkyl group having from 1 to 5 carbon atoms and each of n and m independently has a value of from 0 to 100; and (b) a propellant can be used as aerosols.

9 Claims, No Drawings

OTHER PUBLICATIONS

Kirk-Othmer, Encyclopedia of Chemical Technology, 4th Edition, vol. 22, pp. 670-691.
B. Elvers, et al. (Eds.), Ullmann's Encyclopedia of Industrial Chemistry, 5th Edition, vol. A12, pp. 581-583.
A.G. Shaikh, et al., "Organic Carbonates", Chem. Rev., vol. 96, No. 3, (1996), pp. 951-976.
C. Todd, et al., "Volatile silicone fluids for cosmetic formulations", Cosmetics and Toiletries, vol. 91, (Jan., 1976), pp. 29-32.
R. Lochhead et al., "Encyclopedia of Polymers and Thickeners for Cosmetics", Cosmetics & Toiletries, vol. 108, (May, 1993), pp. 95-114, 116-124, 127-130, 132-135.

* cited by examiner

AEROSOLS

FIELD OF THE INVENTION

This invention relates to deodorizing preparations containing dialkyl carbonates and propellents and to their use as aerosols.

PRIOR ART

Aerosols or sprays are distinguished not only by their easy handling, convenient "dosability" and hygienic use, but also by the uniform effectiveness of their contents sealed off from the outside atmosphere. For this reason, aerosols have become so widespread in a few years as an application for cosmetics, household and industrial products that they are hardly any groups of active substances which cannot be applied as sprays (Aerosol Spray Report 36, NO. 3, 10 et seq. (1997), Aerosol Spray Report 36, No. 9, 80 et seq. (1997), Aerosol Spray Report 36, No. 6, 34 et seq. (1997), general: Kirk-Othmer (4) 1, 670-685; 22, 670-691, Ullmann (4) 2, 254-259; 7, 114-118; (5) A 12, 581-583 I, see also Aerosols.—for journals and organizations, see Aerosols). Only a few oil components, such as isopropyl myristate and cyclomethicone for example, can be incorporated in hitherto known aerosol formulations.

Accordingly, the problem addressed by the present invention was to provide new oil components which could be mixed with known propellents, preferably butane and/or propane and derivatives thereof, and thus used as aerosols. In addition, such aerosol mixtures would also allow the incorporation of active substances, such as for example perfume, vitamins, deodorants, etc.

DESCRIPTION OF THE INVENTION

The present invention relates to cosmetic and/or pharmaceutical preparations containing
(a) dialkyl carbonates corresponding to formula (I):

$$R^1O(CH_2CH_2O)_n\text{---}\overset{O}{\underset{\|}{C}}(OCH_2CH_2)_m\text{---}OR^2 \quad (I)$$

in which $R^1$ is a linear alkyl and/or alkenyl group containing 6 to 22 carbon atoms, a 2-ethylhexyl, isotridecyl or isostearyl group or a group derived from a polyol containing 2 to 15 carbon atoms and at least two hydroxyl groups, $R^2$ has the same meaning as $R^1$ or is an alkyl group containing 1 to 5 carbon atoms and n and m independently of one another stand for 0 or numbers of 1 to 100, and
(b) propellents.

It has surprisingly been found that aerosol preparations which allow the incorporation of dialkyl carbonates and complete mixing with known propellents can be produced. According to the invention, therefore, aerosols in which the molar ratio of propellent to dialkyl carbonate is 1:1 can also be obtained. In addition, perfume oils, UV filters, deodorants and other additives, which may be added according to the application envisaged, can be dissolved or solubilized particularly well and homogeneously in aerosols containing dialkyl carbonates. Another advantageous effect is that aerosols containing dialkyl carbonates, more especially dioctyl and dihexyl carbonates, have a particularly dry feeling on the skin.

Aerosols

Aerosols or sprays are known to be spraying devices with a filling of liquid, paste-like or powder-form substances which are under the pressure of a propellent or a propellant gas. The containers are equipped with valves differing widely in design which enable the contents to be removed as a mist, smoke, foam, powder, paste or liquid jet. The active substance solution, which in the present case contains the dialkyl carbonate(s) and optionally other active principles, i.e. the product to be sprayed, is mixed with liquid propellent. Above this mixture stands gaseous propellent which applies a uniform pressure to all sides, including the surface of the liquid active substance/propellent mixture. When pressure is applied to the button, the valve opens. The active substance/propellent mixture is forced upwards through the riser by the propellant gas and leaves the can through the valve. The propellent mixed with the active substance solution evaporates immediately and the active substance solution is converted into a very fine mist (atomization) or forms a fine-cell foam. Information on the technology of spray production etc. can be found in the relevant prior art literature. The particle size—one of the most important parameters for sprays—is determined with the aid of specially developed instruments or by holography, light scattering, radioactive marking, etc. The production, testing and storage of spray cans are subject to certain rules and regulations (Technical Rules For Pressurized Gases and Pressurized Containers).

The pressurized gas containers used are, above all, cylindrical containers of metal (aluminium, tin plate <1,000 ml), protected or shatterproof glass or plastic (<220 ml) or shattering glass or plastic (<150 ml), selection parameters including compressive strength and fracture resistance, corrosion resistance, easy fillability, optionally sterilizability, etc. and also aesthetic aspects, handiness, printability, etc. (cf. Römpp Lexikon Chemie—Version 2.0, Stuttgart/New York; Georg Thieme Verlag 1999).

Dialkyl Carbonates

Dialkyl carbonates which form component (a) are basically known compounds even through some of the claimed compounds are being described for the first time in the present specification. Basically, they may be prepared by transesterification of dimethyl or diethyl carbonate with the hydroxy compounds mentioned using known methods. A review of these methods can be found, for example, in Chem. Rev. 96, 951 (1996). Dialkyl carbonates corresponding to formula (I) which are particularly suitable for solving the stated problem satisfy one of the following requirements:

(A) $R^1$ is a linear alkyl group containing 6 to 18, preferably 6 to 16 and more particularly 8 to 10 carbon atoms or a 2-ethylhexyl group and $R^2$ has the same meaning as $R^1$ or represents methyl;

(B) $R^1$ is a linear alkyl group containing 12 to 18 carbon atoms, $R^2$ has the same meaning as $R^1$ or represents methyl and n and m stand for numbers of 1 to 10;

(C) $R^1$ is a residue of a polyol selected from the group consisting of glycerol, alkylene glycols, technical oligoglycerol mixtures, methylol compounds, lower alkyl glucosides, sugar alcohols, sugars and aminosugars and $R^2$ has the same meaning as $R^1$ or represents a linear or branched alkyl group containing 8 to 12 carbon atoms or methyl.

Typical examples of dialkyl carbonates belonging to the two groups (A) and (B) are complete or partial transesterification products of dimethyl and/or diethyl carbonate with caproic alcohol, caprylic alcohol, 2-ethylhexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol and the technical mixtures thereof formed, for example, in the high-pressure hydrogenation of technical methyl esters based on fats and oils or aldehydes from Roelen's oxosynthesis and as monomer fraction in the dimerization of unsaturated fatty alcohols. The transesterification products of the lower carbonates with the alcohols mentioned in the form of their adducts with 1 to 100, preferably 2 to 50 and more preferably 5 to 20 mol ethylene oxide are also suitable. Di-n-octyl carbonates are preferred. Dioctyl or dihexyl carbonates are preferably used.

The carbonates of group (C) are being described for the first time in the present specification. They are compounds which are obtained by complete or partial transesterification of dimethyl and/or diethyl carbonate with polyols. Polyols suitable for the purposes of the invention preferably contain 2 to 15 carbon atoms and at least two hydroxyl groups. Typical examples are glycerol;

alkylene glycols such as, for example, ethylene glycol, diethylene glycol, propylene glycol, butylene glycol, hexylene glycol and also polyethylene glycols with an average molecular weight of 100 to 1,000 dalton;

technical oligoglycerol mixtures with a degree of self-condensation of 1.5 to 10, for example technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, more particularly those containing 1 to 8 carbon atoms in the alkyl group, for example methyl and butyl glucoside;

sugar alcohols containing 5 to 12 carbon atoms such as, for example, sorbitol or mannitol;

sugars containing 5 to 12 carbon atoms such as, for example, glucose or sucrose and aminosugars such as, for example, glucamine.

This reaction can of course not only result in replacement of a methyl or ethyl group by a polyol residue, it also gives a mixture in which several hydroxy groups or even all the hydroxyl groups of the polyol are attached to carbonate groups so that an oligomeric or polymeric net structure may even be obtained. In the context of the invention, compounds of this type are also meant to fall within the scope of general formula (I).

The preparations according to the invention may contain the dialkyl carbonates, preferably dioctyl and/or dihexyl carbonate and more especially di-n-octyl carbonate, in quantities of 1 to 50, preferably 3 to 25 and more particularly 5 to 15% by weight, based on the final composition.

Propellents

Suitable propellents are any propellents known to the expert which represent liquefied or compressed gases such as, for example, dimethyl ether, carbon dioxide, chlorofluorocarbons (CFCs), nitrogen oxides and pentane, butane and propane and/or isomers thereof. Here, too, the choice is governed by the product to be sprayed or the application envisaged. Where compressed gases, such as nitrogen, carbon dioxide or dinitrogen oxide which are generally insoluble in the liquid contents of the spray are used, the operating pressure falls each time the value is actuated. Propellents such as these are suitable above all for water-based products and for products which do not require particularly fine atomization, for example toothpastes, hand creams, sun protection products, fruit juice concentrates and concentrated seasonings, whipped cream (where only $N_2O$ optionally in combination with $CO_2$ is allowed), pharmaceutical sprays (where $N_2O$ is unsuitable because of the anaesthetization risk), spray cleaners, lubricants and polishes. Liquefied gases soluble in the active substance itself or even acting a solvent themselves offer the advantage as propellents of a uniform operating pressure and uniform distribution, because the propellent evaporates instantaneously in air and in doing so occupies several hundred times the volume so that the (solid or liquid) active substance is dispersed much more finely. A cooling effect often undesirable for cosmetic sprays where liquefied gases are used can be partly obviated by choosing suitable mixing ratios.

The CFCs particularly suitable as propellents have now very largely been replaced since their harmful effect on the ozone layer was discovered. Accordingly, mixtures of propane and butane, occasionally with dimethyl ether, are preferably used (Römpp Lexikon Chemie—Version 2.0, Stuttgart/New York; Georg Thieme Verlag 1999).

The preparations according to the invention may contain the propellents in quantities of 3 to 95, preferably 5 to 75, more preferably 20 to 65 and most preferably 30 to 50% by weight, based on the final composition.

Commercial Applications

The present invention also relates to the use of the preparations according to the invention as aerosols, more especially cosmetic aerosols. However, the preparations according to the invention are suitable for any applications known to the expert for aerosols, preferably in the home (for example for cleaning, etc.), but also in the institutional and industrial sectors.

In a preferred embodiment of the invention, the compositions may contain components (a) and (b) preferably in the following quantities, based on the final composition:

(a) 1 to 50, preferably 3 to 25 and more particularly 5 to 15% by weight dialkyl carbonates, (b) 3 to 95, preferably 5 to 75, more preferably 20 to 65 and most preferably 30 to 50% by weight propellent and optionally (c) 0 to 30, preferably 1 to 20 and more particularly 4 to 12% by weight, with the proviso that the quantities shown add up to 100% by weight with water and are based on the final composition.

In a preferred embodiment of the invention, the molar ratio of dialkyl carbonate to propellent is 1:5 to 1:1 and more particularly 1:3 to 1:1.5. In another preferred embodiment of the invention, other auxiliaries and additives (see below) may also be used, including for example polymers, silicone compounds, lecithins, phospholipids, biogenic agents, UV protection factors, antioxidants, deodorants, antiperspirants, antidandruff agents, film formers, insect repellents, self-tanning agents, tyrosine inhibitors, hydrotropes, solubilizers, preservatives, perfume oils and dyes and the like, preferably UV protection factors, self-tanning agents, deodorants, antidandruff agents, biogenic agents, insect repellents, dyes and perfume oils. In a preferred embodiment of the invention, the molar ratio of dialkyl carbonate to the above-mentioned additives is 10:1 to 1:10, preferably 5:1 to 1:5 and more particularly 3:1 to 1:3. Corresponding mixtures show good miscibility with the propellents according to the invention.

Auxiliaries and Additives

These preparations may also contain mild surfactants, oil components, emulsifiers, consistency factors, thickeners, superfatting agents, stabilizers, polymers, silicone compounds, fats, waxes, lecithins, phospholipids, biogenic agents, UV protection factors, antioxidants, deodorants, antiperspirants, antidandruff agents, film formers, swelling agents, insect repellents, self-tanning agents, tyrosine inhibitors (depigmenting agents), hydrotropes, solubilizers, preservatives, perfume oils, dyes and the like as further auxiliaries and additives.

Surfactants

Suitable surfactants are anionic, nonionic, cationic and/or amphoteric or zwitterionic surfactants. Typical examples of anionic surfactants are soaps, alkyl benzenesulfonates, alkanesulfonates, olefin sulfonates, alkylether sulfonates, glycerol ether sulfonates, α-methyl ester sulfonates, sulfofatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl(ether) phosphates. If the anionic surfactants contain polyglycol ether chains, they may have a conventional homolog distribution although they preferably have a narrow-range homolog distribution. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partly oxidized alk(en)yl oligoglycosides or glucuronic acid derivatives, fatty acid-N-alkyl glucamides, protein hydrolyzates (particularly wheat-based vegetable products), polyol fatty acid esters, sugar esters, sorbitan esters, polysorbates and amine oxides. If the nonionic surfactants contain polyglycol ether chains, they may have a conventional homolog distribution, although they preferably have a narrow-range homolog distribution. Typical examples of cationic surfactants are quaternary ammonium compounds, for example dimethyl distearyl ammonium chloride, and esterquats, more particularly quaternized fatty acid trialkanolamine ester salts. Typical examples of amphoteric or zwitterionic surfactants are alkylbetaines, alkylamidobetaines, aminopropionates, aminoglycinates, imidazolinium betaines and sulfobetaines. The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside und Mineralöladditive (Catalysts, Surfactants and Mineral Oil Additives)", Thieme Verlag, Stuttgart, 1978, pages 123-217. Typical examples of particularly suitable mild, i.e. particularly dermatologically compatible, surfactants are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, α-olefin sulfonates, ether carboxylic acids, alkyl oligoglucosides, fatty acid glucamides, alkylamidobetaines, amphoacetals and/or protein fatty acid condensates, preferably based on wheat proteins.

Oil Components

Suitable other oil components are, for example, Guarbet alcohols based on fatty alcohols containing 6 to 18 and preferably 8 to 10 carbon atoms, esters of linear $C_{6-22}$ fatty acids with linear or branched $C_{6-22}$ fatty alcohols or esters of branched $C_{6-13}$ carboxylic acids with linear or branched $C_{6-22}$ fatty alcohols such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate. cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl bahenate and erucyl erucate. Also suitable are esters of linear $C_{6-22}$ fatty acids with branched alcohols, more particularly 2-ethyl hexanol, esters of $C_{18-38}$ alkyihydroxycarboxylic acids with linear or branched $C_{6-22}$ fatty alcohols (cf. DE 19756377 A1), more especially Dioctyl Malate, esters of linear and/or branched fatty acids with polyhydric alcohols (for example propylene glycol, dimer diol or trimer triol) and/or Guerbet alcohols, triglycerides based on $C_{6-10}$ fatty acids, liquid mono-, di- and triglyceride mixtures based on $C_{6-18}$ fatty acids (cf. WO97/29170), esters of $C_{8-22}$ fatty alcohols and/or Guerbet alcohols with aromatic carboxylic acids, more particularly benzoic acid, esters of $C_{2-12}$ dicarboxylic acids with linear or branched alcohols containing 1 to 22 carbon atoms or polyols containing 2 to 10 carbon atoms and 2 to 6 hydroryl groups, vegetable oils, branched primary alcohols, substituted cyclohexanes, Guerbet carbonates, esters of benzoic acid with linear and/or branched $C_{5-22}$ alcohols (for example Finsolv® TN), linear or branched, symmetrical or nonsymmetrical dialkyl ethers containing 6 to 22 carbon atoms per alkyl group, such as Dicaprylyl Ether (Cetiol® OE), ring opening products of epoxidized fatty acid esters with polyols, silicone oils (cyclomethicone, silicon methicone types, etc.) and/or aliphatic or naphthenic hydrocarbons, for example squalane. squalene or dialkyl cyclohexanes.

Emulsifiers

Suitable emulsifiers are, for example, nonionic surfactants from at least one of the following groups:
  products of the addition of 2 to 30 mol ethylene oxide and/or 0 to 5 mol propylene oxide onto linear $C_{8-22}$ fatty alcohols, $C_{12-22}$ fatty acids, alkyl phenols containing 8 to 15 carbon atoms in the alkyl group and alkylamines containing 8 to 22 carbon atoms in the alkyl group;
  alkyl and/or alkenyl oligoglycosides containing 8 to 22 carbon atoms in the alk(en)yl group and ethoxylated analogs thereof;
  addition products of 1 to 15 mol ethylene oxide onto castor oil and/or hydrogenated castor oil;
  addition products of 15 to 60 mol ethylene oxide onto castor oil and/or hydrogenated castor oil;
  partial esters of glycerol and/or sorbitan with unsaturated, linear or saturated, branched fatty acids containing 12 to 22 carbon atoms and/or hydroxycarboxylic acids containing 3 to 18 carbon atoms and adducts thereof with 1 to 30 mol of ethylene oxide;
  partial esters of polyglycerol (average degree of self-condensation 2 to 8), polyethylene glycol (molecular weight 400 to 5,000), trimethylolpropane, pentaerythritol, sugar alcohols (for example sorbitol), alkyl glucosides (for example methyl glucoside, butyl glucoside, lauryl glucoside) and polyglucosides (for example cellulose) with saturated and/or unsaturated, linear or branched fatty acids containing 12 to 22 carbon atoms and/or hydroxycarboxylic acids containing 3 to 18 carbon atoms and adducts thereof with 1 to 30 mol ethylene oxide;

mixed esters of pentaerythritol, fatty acids, citric acid and fatty alcohol according to DE 1165574 PS and/or mixed esters of fatty acids containing 6 to 22 carbon atoms, methyl glucose and polyols, preferably glycerol or polyglycerol, mono-, di- and trialkyl phosphates and mono-, di- and/or tri-PEG-alkyl phosphates and salts thereof, wool wax alcohols, polysiloxane/polyalkyl/polyether copolymers and corresponding derivatives, block copolymers, for example Polyethyleneglycol-30 Dipolyhydroxystearate;

polymer emulsifiers, for example Pemulen types (TR-1, TR-2) of Goodrich;

polyalkylene glycols and glycerol carbonate.

The addition products of ethylene oxide and/or propylene oxide onto fatty alcohols, fatty acids, alkylphenols or onto castor oil are known commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of adducts of ethylene oxide onto glycerol are known as refatting agents for cosmetic formulations from DE 2024051 PS.

Alkyl and/or alkenyl oligoglycosides, their production and their use are known from the prior art. They are produced in particular by reacting glucose or oligosaccharides with primary alcohols containing 8 to 18 carbon atoms. So far as the glycoside unit is concerned, both monoglycosides in which a cyclic sugar unit is attached to the fatty alcohol by a glycoside bond and oligomeric glycosides with a degree of oligomerization of preferably up to about 8 are suitable. The degree of oligomerization is a statistical mean value on which the homolog distribution typical of such technical products is based.

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30 and preferably 5 to 10 mol ethylene oxide onto the partial glycerides mentioned are also suitable.

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable.

Typical examples of suitable polyglycerol esters are Polyglyceryl-2 Dipolyhydroxystearate (Dehymuls® PGPH), Polyglycerin-3-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Polyglyceryl-3 Methylglucose Distearate (Tego Care® 450), Polyglyceryl-3 Beeswax (Cera Bellina®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof. Examples of other suitable polyolesters are the mono-, di- and triesters of trimethylolpropane or pentaerythritol with lauric acid, coconuffatty acid, tallow fatty acid, palmitic acid, stearic acid, oleic acid, behenic acid and the like optionally reacted with 1 to 30 mol ethylene oxide.

Other suitable emulsifiers are zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in, the alkyl group. Particularly preferred ampholytic surfactants are N-cocoalkylaminopropionate, cocoacylaminoethyl aminopropionate and $C_{12/18}$ acyl sarcosine. Finally, cationic surfactants are also suitable emulsifiers, those of the esterquat type, preferably methyl-quaternized difatty acid triethanolamine ester salts, being particularly preferred.

Fats and Waxes

Typical examples of fats are glycerides, i.e. solid or liquid, vegetable or animal products which consist essentially of mixed glycerol esters of higher fatty acids. Suitable waxes are inter alia natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes. Besides the fats, other suitable additives are fat-like substances, such as lecithins and phospholipids. Lecithins are known among experts as glycerophospholipids which are formed from fatty acids, glycerol, phosphoric acid and choline by esterification. Accordingly, lecithins are also frequently referred to by experts as phosphatidyl cholines (PCs) and correspond to the following general formula:

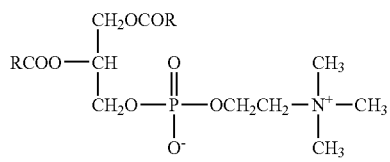

where R typically represents linear aliphatic hydrocarbon radicals containing 15 to 17 carbon atoms and up to 4 cis-double bonds. Examples of natural lecithins are the kephalins which are also known as phosphatidic acids and which are derivatives of 1,2-diacyl-sn-glycerol-3-phosphoric acids. By contrast, phospholipids are generally understood to be mono- and preferably diesters of phosphoric acid with glycerol (glycero-phosphates) which are normally classed as fats. Sphingosines and sphingolipids are also suitable.

Consistency Factors and Thickeners

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used. Suitable thickeners are, for example, Aerosil® types (hydrophilic silicas), polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® and Pemulen types [Goodrich]; Synthalens® [Sigma]; Keltrol types [Kelco]; Sepigel types [Seppic]; Salcare types [Allied Colloids]), polyacrylamides, polymers, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates or alkyl oligoglucosides and electrolytes, such as sodium chloride and ammonium chloride.

Superfatting Agents

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

Stabilizers

Metal salts of fatty acids such as, for example, magnesium, aluminium and/or zinc stearate or ricinoleate may be used as stabilizers.

Polymers

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, amodimethicone, copolymers of adipic acid and dimethylaminohydroxypropyl diethylenetriamine (Cartaretine®, Sandoz), copolymers of acrylic acid with dimethyl diallyl ammonium chloride (Merquat® 550, Chemviron), polyaminopolyamides as described, for example, in FR 2252840 A and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar®CBS, Jaguar®C-17, Jaguar®C-16 of Celanese, quaternized ammonium salt polymers such as, for example, Mirapol® A-15, Mirapol® AD-1, Mirapol® AZ-1 of Miranol.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamido-propyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones. Other suitable polymers and thickeners can be found in Cosmetics & Toiletries, Vol. 108, May 1993, pages 95 et seq.

Silicone Compounds

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates. A detailed overview of suitable volatile silicones can be found in Todd et al. in Cosm. Toil. 91, 27 (1976).

UV Protection Factors and Antioxidants

UV protection factors in the context of the invention are, for example, organic substances (light filters) which are liquid or crystalline at room temperature and which are capable of absorbing ultraviolet radiation and of releasing the energy absorbed in the form of longer-wave radiation, for example heat. UV-B filters can be oil-soluble or water-soluble. The following are examples of oil-soluble substances:

3-benzylidene camphor or 3-benzylidene norcamphor and derivatives thereof, for example 3-(4-methylbenzylidene)-camphor as described in EP 0693471 B1;

4-aminobenzoic acid derivatives, preferably 4-(dimethylamino)-benzoic acid-2-ethylhexyl ester, 4-(dimethylamino)-benzoic acid-2-octyl ester and 4-(dimethylamino)-benzoic acid amyl ester;

esters of cinnamic acid, preferably 4-methoxycinnamic acid-2-ethylhexyl ester, 4-methoxycinnamic acid propyl ester, 4-methoxycinnamic acid isoamyl ester, 2-cyano-3,3-phenylcinnamic acid-2-ethylhexyl ester (Octocrylene);

esters of salicylic acid, preferably salicylic acid-2-ethylhexyl ester, salicylic acid-4-isopropylbenzyl ester, salicylic acid homomenthyl ester;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably 4-methoxybenzalmalonic acid di-2-ethylhexyl ester;

triazine derivatives such as, for example, 2,4,6-trianilino-(p-carbo-2'-ethyl-1'-hexyloxy)-1,3,5-triazine and Octyl Triazone as described in EP 0818450 A1 or Dioctyl Butamido Triazone (Uvasorb® HEB);

propane-1,3-diones such as, for example, 1-(4-tert.butylphenyl)-3-(4'-methoxyphenyl)-propane-1,3-dione;

ketotricyclo(5.2.1.0)decane derivatives as described in EP 0694521 B1.

Suitable water-soluble substances are 2-phenylbenzimidazole-5-sulfonic acid and alkali metal, alkaline earth metal, ammonium, alkylammonium, alkanolammonium and glucammonium salts thereof;

sulfonic acid derivatives of benzophenones, preferably 2-hydroxy-4-methoxybenzophenone-5-sulfonic acid and salts thereof;

sulfonic acid derivatives of 3-benzylidene camphor such as, for example, 4-(2-oxo-3-bornylidenemethyl)-benzene sulfonic acid and 2-methyl-5-(2-oxo-3-bornylidene)-sulfonic acid and salts thereof.

Typical UV-A filters are, in particular, derivatives of benzoyl methane such as, for example, 1-(4'-tert.butylphenyl)-3-(4'-methoxyphenyl)-propane-1,3-dione, 4-tert.butyl-4'-methoxydibenzoyl methane (Parsol 1789), 1-phenyl-3-(4'-isopropylphenyl)-propane-1,3-dione and the enamine compounds described in DE 19712033 A1 (BASF). The UV-A and UV-B filters may of course also be used in the form of mixtures. Particularly favorable combinations consist of the derivatives of benzoyl methane, for example 4-tert.butyl-4'-methoxydibenzoylmethane (Parsol 1789) and 2-cyano-3, 3-phenylcinnamic acid-2-ethylhexyl ester (Octocrylene) in combination with esters of cinnamic acid, preferably 4-methoxycinnamic acid-2-ethylhexyl ester and/or 4-methoxycinnamic acid propyl ester and/or 4-methoxycinnamic acid isoamyl ester. Mixtures such as these are advantageously combined with water-soluble filters such as, for example, 2-phenylbenzimidazole-5-sulfonic acid and alkali metal, alkaline earth metal, ammonium, alkylammonium, alkanolammonium and glucammonium salts thereof.

Besides the soluble substances mentioned, insoluble UV protection pigments, i.e. finely dispersed metal oxides or salts, may also be used for this purpose. Examples of suitable metal oxides are, in particular, zinc oxide and titanium dioxide and also oxides of iron, zirconium, silicon, manganese, aluminium and cerium and mixtures thereof. Silicates (talcum), barium sulfate and zinc stearate may be used as salts. The oxides and salts are used in the form of the pigments for skin-care and skin-protecting emulsions and decorative cosmetics. The particles should have a mean diameter of less than 100 nm, preferably between 5 and 50 nm and more preferably between 15 and 30 nm. They may be spherical in shape although ellipsoidal particles or other non-spherical particles may also be used. The pigments may also be surface-treated, i.e. hydrophilicized or hydrophobicized. Typical examples are coated titanium dioxides, for example Titandioxid T 805 (Degussa) and Eusolex® T2000 (Merck). Suitable hydrophobic coating materials are, above all, silicones and, among these, especially trialkoxyoctylsilanes or dimethicones. So-called micro- or nanopigments are preferably used in sun protection products. Micronized zinc oxide is preferably used. Other suitable UV filters can be found in P. Finkel's review in SÖFW-Journal 122, 543 (1996) and in Parfümerie und Kosmetik 3 (1999), pages 11 et seq.

Besides the two groups of primary sun protection factors mentioned above, secondary sun protection factors of the antioxidant type may also be used. Secondary sun protection factors of the antioxidant type interrupt the photochemical reaction chain which is initiated when UV rays penetrate into the skin. Typical examples are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages (for example pmole to μmole/kg), also (metal) chelators (for example α-hydroxyfatty acids, palmitic acid, phytic acid, lactoferrine), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, α-glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, Superoxid-Dismutase, zinc and derivatives thereof (for example $ZnO$, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

Biogenic Agents

In the context of the invention, biogenic agents are, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes.

Deodorants and Germ Inhibitors

Cosmetic deodorants counteract, mask or eliminate body odors. Body odors are formed through the action of skin bacteria on apocrine perspiration which results in the formation of unpleasant-smelling degradation products. Accordingly, deodorants contain active principles which act as germ inhibitors, enzyme inhibitors, odor absorbers or odor maskers. Basically, suitable germ inhibitors are any substances which act against gram-positive bacteria such as, for example, 4-hydroxybenzoic acid and salts and esters thereof, N-(4-chlorophenyl)-N'-(3,4-dichlorophenyl)-urea, 2,4,4'-trichloro-2'-hydroxydiphenylether (triclosan), 4-chloro-3,5-dimethylphenol, 2,2'-methylene-bis-(6-bromo-4-chlorophenol), 3-methyl-4-(1-methylethyl)-phenol, 2-benzyl-4-chlorophenol, 3-(4-chlorophenoxy)-propane-1,2-diol, 3-iodo-2-propinyl butyl carbamate, chlorhexidine, 3,4,4'-trichlorocarbanilide (TTC), antibacterial perfumes, thymol, thyme oil, eugenol, clove oil, menthol, mint oil, farnesol, phenoxyethanol, glycerol monocaprate, glycerol monocaprylate, glycerol monolaurate (GML), diglycerol monocaprate (DMC), salicylic acid-N-alkylamides such as, for example, salicylic acid-n-octyl amide or salicylic acid-n-decyl amide.

Suitable enzyme inhibitors are, for example, esterase inhibitors. Esterase inhibitors are preferably trialkyl citrates, such as trimethyl citrate, tripropyl citrate, triisopropyl citrate, tributyl citrate and, in particular, triethyl citrate (Hydagen® CAT, Henkel KGaA, Düsseldorf, FRG). Esterase inhibitors inhibit enzyme activity and thus reduce odor formation. Other esterase inhibitors are sterol sulfates or phosphates such as, for example, lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof, for example citric acid, malic acid, tartaric acid or tartaric acid diethyl ester, and zinc glycinate.

Suitable odor absorbers are substances which are capable of absorbing and largely retaining the odor-forming compounds. They reduce the partial pressure of the individual components and thus also reduce the rate at which they spread. An important requirement in this regard is that perfumes must remain unimpaired. Odor absorbers are not active against bacteria. They contain, for example, a complex zinc salt of ricinoleic acid or special perfumes of largely neutral odor known to the expert as "fixateurs" such as, for example, extracts of labdanum or styrax or certain abietic acid derivatives as their principal component. Odor maskers are perfumes or perfume oils which, besides their odor-masking function, impart their particular perfume note to the deodorants. Suitable perfume oils are, for example, mixtures of natural and synthetic fragrances. Natural perfumes include the extracts of blossoms, stems and leaves, fruits, fruit peel, roots, woods, herbs and grasses, needles and branches, resins and balsams. Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, p-tert.butyl cyclohexylacetate, linalyl acetate, phenyl ethyl acetate, linalyl benzoate, benzyl formate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetivert oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Antiperspirants reduce perspiration and thus counteract underarm wetness and body odor by influencing the activity of the eccrine sweat glands. Aqueous or water-free antiperspirant formulations typically contain the following ingredients:

astringent active principles,
oil components,
nonionic emulsifiers,
co-emulsifiers,
consistency factors,
auxiliaries in the form of, for example, thickeners or complexing agents and/or
non-aqueous solvents such as, for example, ethanol, propylene glycol and/or glycerol.

Suitable astringent active principles of antiperspirants are, above all, salts of aluminium, zirconium or zinc. Suitable antihydrotic agents of this type are, for example, aluminium chloride, aluminium chlorohydrate, aluminium dichlorohydrate, aluminium sesquichlorohydrate and complex compounds thereof, for example with 1,2-propylene glycol, aluminium hydroxyaliantoinate, aluminium chloride tartrate, aluminium zirconium trichlorohydrate, aluminium zirconium tetrachlorohydrate, aluminium zirconium pentachlorohydrate and complex compounds thereof, for example with amino acids, such as glycine. Oil-soluble and water-soluble auxiliaries typically encountered in antiperspirants may also be present in relatively small amounts. Oil-soluble auxiliaries such as these include, for example, inflammation-inhibiting, skin-protecting or pleasant-smelling essential oils,
synthetic skin-protecting agents and/or
oil-soluble perfume oils.

Typical water-soluble additives are, for example, preservatives, water-soluble perfumes, pH regulators, for example buffer mixtures, water-soluble thickeners, for example water-soluble natural or synthetic polymers such as, for example, xanthan gum, hydroxyethyl cellulose, polyvinyl pyrrolidone or high molecular weight polyethylene oxides.

Film Formers

Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

Antidandruff Agents

Suitable antidandruff agents are Pirocton Olamin (1-hydroxy-4-methyl-6-(2,4,4-trimethylpentyl)-2-(1H)-pyridinone monoethanolamine salt), Baypival® (Climbazole), Ketoconazol® (4-acetyl-1-{4-[2-(2,4-dichlorophenyl)r-2-(1H-imidazol-1-ylmethyl)-1,3-dioxylan-c4-ylmethoxyphenyl}-piperazine, selenium disulfide, colloidal sulfur, sulfur polyethylene glycol sorbitan monooleate, sulfur ricinol polyethoxylate, sulfur tar distillate, salicylic acid (or in combination with hexachlorophene), undecylenic acid, monoethanolamide sulfosuccinate Na salt, Lamepon® UD (protein/undecylenic acid condensate), zinc pyrithione, aluminium pyrithione and magnesium pyrithione/dipyrithione magnesium sulfate.

Swelling Agents

Suitable swelling agents for aqueous phases are montmorillonites, clay minerals, Pemulen and alkyl-modified Carbopol types (Goodrich). Other suitable polymers and swelling agents can be found in R. Lochhead's review in Cosm. Toil. 108, 95 (1993).

Insect Repellents

Suitable insect repellents are N,N-diethyl-m-toluamide, pentane-1,2-diol or Ethyl Butylacetylaminopropionate.

Self-tanning Agents and Depigmenting Agents

A suitable self-tanning agent is dihydroxyacetone. Suitable tyrosine inhibitors which prevent the formation of melanin and are used in depigmenting agents are, for example, arbutin, koji acid, coumaric acid and ascorbic acid (vitamin C).

Hydrotropes

In addition, hydrotropes, for example ethanol, isopropyl alcohol or polyols, may be used to improve flow behavior. Suitable polyols preferably contain 2 to 15 carbon atoms and at least two hydroxyl groups. The polyols may contain other functional groups, more especially amino groups, or may be modified with nitrogen. Typical examples are

- glycerol;
- alkylene glycols such as, for example, ethylene glycol, diethylene glycol, propylene glycol, butylene glycol, hexylene glycol and polyethylene glycols with an average molecular weight of 100 to 1000 dalton;
- technical oligoglycerol mixtures with a degree of self-condensation of 1.5 to 10 such as, for example, technical diglycerol mixtures with a diglycerol content of 40 to 50% by weight;
- methylol compounds such as, in particular, trimethylol ethane, trimethylol propane, trimethylol butane, pentaerythritol and dipentaerythritol;
- lower alkyl glucosides, particularly those containing 1 to 8 carbon atoms in the alkyl group, for example methyl and butyl glucoside;
- sugar alcohols containing 5 to 12 carbon atoms, for example sorbitol or mannitol,
- sugars containing 5 to 12 carbon atoms, for example glucose or sucrose;
- amino sugars, for example glucamine;
- dialcoholamines, such as diethanolamine or 2-aminopropane-1,3-diol.

Preservatives

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive").

Perfume Oils

Suitable perfume oils are mixtures of natural and synthetic perfumes. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamom, costus, iris, calmus), woods (pinewood, sandalwood, guaiac wood, cedarwood, rosewood), herbs and grasses (tarragon, lemon, grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, α-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable perfume. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetivert oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Dyes

Suitable dyes are any of the substances suitable and approved for cosmetic purposes as listed, for example, in the publication "Kosm tische Färbemittel" of the Farbstoffkommission der Deutschen Forschungsgemeinschaft, Verlag Chemie, Weinheim, 1984, pages 81 to 106. These dyes are normally used in concentrations of 0.001 to 0.1% by weight, based on the mixture as a whole.

The total percentage content of auxiliaries and additives may be from 0 to 30% by weight and is preferably from 1 to 20% by weight and more particularly from 4 to 12% by weight, based on the final concentration. The preparations may be produced by standard hot or cold processes and are preferably produced by the phase inversion temperature method.

EXAMPLES

The solubility (solubilization) (+=thorough mixing; −=separation) of the oil component according to the invention (Examples 1 to 6; Table 1) and the propellent butane is shown in the following Table against that of the comparison oil component (C1 to C3). In addition, the subjective skin feel was evaluated by a panel of 5 examiners (tt=very dry, t=dry). The results are set out in Tables 1 and 2.

TABLE 1

Miscibility of the aerosol preparations with dialkyl carbonates (quantities in % by weight)

| Component | 1 | 2 | 3 | 4 | 5 | 6 | C1 | C2 | C3 |
|---|---|---|---|---|---|---|---|---|---|
| Cetiol CC Di-n-octylcarbonate | 50 | 25 | 43 | 15 | 8 | 20 | — | — | — |
| IPM/IPM-PH Isopropyl Myristate | — | — | — | — | — | — | 50 | 20 | — |
| Cetiol OE Di-n-octyl ether | — | — | — | — | — | — | — | — | 25 |
| Butane | 50 | 72 | 55 | 85 | 50 | 75.9 | 50 | 75.9 | 72 |
| Perfume | — | 3 | — | — | — | 1 | — | 1 | 3 |
| Aluminium chlorohydrate | — | — | 2 | — | — | 3 | — | 3 | — |
| Chitosan | — | — | — | — | — | 0.1 | — | 0.1 | — |
| Solubilization | + | + | + | + | + | + | + | + | — |
| Skin feel | tt | tt | tt | tt | tt | tt | t | t | t |

TABLE 2

Spray preparations - compositions and properties (quantities in % by weight)

| Component | 1 | 2 | 3 | C1 | C2 |
|---|---|---|---|---|---|
| Cetiol ® CC Di-n-octylcarbonate | 8 | 18 | 8 | — | — |
| IPM/IPM-PH Isopropyl Myristate | — | — | — | 18 | 8 |
| Aluminium Chlorohydrate | 3 | — | — | — | 3 |
| Miglycol Gel B Caprylic/Capric Triglyceride (and) Stearalkonium Hectorite (and) Propylene Carbonate | 4 | 4 | — | 4 | 4 |
| Cetiol OE Dioctylether | 5 | — | — | — | 5 |
| Cetiol B Di-n-butyl adipate | 6 | — | — | — | 6 |
| Hydagen DCMF (sol. 4%) Chitosan | 0.3 | — | — | — | 0.3 |
| Profumo Massage Perfume | 1 | 1 | — | 1 | 1 |
| Ethanol | 2 | — | 8 | — | 2 |
| Hydagen CAT Triethyl citrate | 1.5 | — | — | — | 1.5 |
| Parsol MCX Ethylhexyl Methoxycinnamate | — | 1 | — | 1 | — |
| Parsol 1789 Butyl Methoxydibenzoylmethane | — | 0.5 | — | 0.5 | — |
| Cyclomethicone | — | — | 10 | — | — |
| Propane/butane | 69.2 | 75.5 | 74 | 75.5 | 69.2 |

(1) Deodorant spray, (2) Sun protection spray, (3) Hair gloss spray

The invention claimed is:

1. A cosmetic and/or pharmaceutical preparation comprising (a) a carbonate of the formula (I):

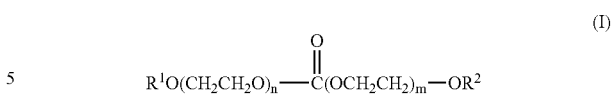

wherein $R^1$ is a linear alkyl and/or alkenyl group having from 6 to 22 carbon atoms, a 2-ethylhexyl, isotridecyl or isostearyl group or a group derived from a polyol having from 2 to 15 carbon atoms and at least two hydroxyl groups; $R^2$ has the same meaning as $R^1$ or is an alkyl group having from 1 to 5 carbon atoms and each of n and m independently has a value of from 0 to 100; and (b) a propellant.

2. The preparation of claim 1 wherein the carbonate comprises at least one of diisooctyl carbonate, dihexyl carbonate and di-n-octyl carbonate.

3. The preparation of claim 2 wherein the dialkyl carbonate comprises di-n-octyl carbonate.

4. The preparation of claim 1 wherein the amount of the carbonate is from 1 to 50% by weight.

5. The preparation of claim 1 wherein the propellant comprises at least one member selected from the group consisting of dimethyl ether, carbon dioxide, a chlorofluorocarbons, a nitrogen oxide, pentane, butane, propane and isomers of pentane, butane and propane.

6. The preparation of claim 5 wherein the amount of the propellant is from 3 to 95% by weight.

7. The preparation of claim 1 further comprising at least one member selected from the group consisting of polymers, silicone compounds, lecithin, phospholipids, biogenic agents, UV protection factors, antioxidants deodorants, antiperspirants, antidandruff agents, film formers, insect repellents, self-tanning agents, tyrosine inhibitors, hydrotropes, solubilizers, preservatives, perfume oils, and dyes.

8. The preparation of claim 1 wherein the mole ratio of component (a) to (b) is from 1:5 to 1:1.

9. A cosmetic and/or pharmaceutical preparation comprising (a) from 1 to 50% by weight of a carbonate of the formula (I):

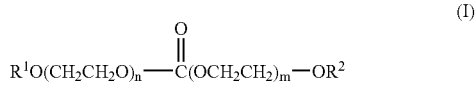

wherein $R^1$ is a linear alkyl and/or alkenyl group having from 6 to 22 carbon atoms, a 2-ethylhexyl, isotridecyl or isostearyl group or a group derived from a polyol having from 2 to 15 carbon atoms and at (east two hydroxyl groups; $R^2$ has the same meaning as $R^1$ or is an alkyl group having from 1 to 5 carbon atoms and each of n and m independently has a value of from 0 to 100; (b) from 3 to 95% by weight of a propellant; and (c) from 0 to 30% by weight of auxiliaries and additives and the remainder water.

* * * * *